(12) United States Patent
Tanaka et al.

(10) Patent No.: US 11,238,978 B2
(45) Date of Patent: Feb. 1, 2022

(54) INFORMATION PROCESSING METHOD, INFORMATION PROCESSING APPARATUS AND NON-TRANSITORY COMPUTER-READABLE RECORDING MEDIUM STORING INFORMATION PROCESSING PROGRAM

(71) Applicant: PANASONIC INTELLECTUAL PROPERTY CORPORATION OF AMERICA, Torrance, CA (US)

(72) Inventors: Toshiaki Tanaka, Hyogo (JP); Hiroya Tanaka, Osaka (JP); Hirofumi Kanai, Osaka (JP); Yuka Yamada, Nara (JP); Yuko Kida, Osaka (JP)

(73) Assignee: PANASONIC INTELLECTUAL PROPERTY CORPORATION OF AMERICA, Torrance, CA (US)

(*) Notice: Subject to any disclaimer, the term of this patent is extended or adjusted under 35 U.S.C. 154(b) by 146 days.

(21) Appl. No.: 16/712,053

(22) Filed: Dec. 12, 2019

(65) Prior Publication Data

US 2020/0194113 A1 Jun. 18, 2020

Related U.S. Application Data

(60) Provisional application No. 62/780,012, filed on Dec. 14, 2018.

(30) Foreign Application Priority Data

Apr. 18, 2019 (JP) .............................. JP2019-079145
Aug. 20, 2019 (JP) .............................. JP2019-150360

(51) Int. Cl.
*G16H 40/20* (2018.01)
*G06Q 40/08* (2012.01)

(52) U.S. Cl.
CPC ............. *G16H 40/20* (2018.01); *G06Q 40/08* (2013.01)

(58) Field of Classification Search
CPC ...... G06Q 10/10; G06Q 10/067; G06Q 40/08; G16H 50/30; G16H 10/60; G16H 40/67; G16H 10/20; G16H 40/20; G16H 50/70; G06F 3/0482; G06F 16/22; G06F 16/2358
See application file for complete search history.

(56) References Cited

U.S. PATENT DOCUMENTS

2018/0122509 A1* 5/2018 Christiansson ........ G16H 10/60

FOREIGN PATENT DOCUMENTS

JP 2002-304470 A 10/2002

* cited by examiner

*Primary Examiner* — Maroun P Kanaan
(74) *Attorney, Agent, or Firm* — Greenblum & Bernstein, P.L.C.

(57) ABSTRACT

An information processing method performed by a computer includes determining a plurality of first support contents corresponding to a care recipient or assistance recipient from a plurality of support contents based on basic information on the care recipient or assistance recipient, outputting first presentation information for presenting the plurality of first support contents and assessment items respectively associated with the plurality of first support contents to a user, determining a second support content from the plurality of first support contents based on assessment results input by the user for the assessment items, and outputting second presentation information for presenting the second support content to the user.

18 Claims, 14 Drawing Sheets

FIG.2

| No. | BASIC GROUP | SUMMARY | AGE | LIVING STATUS | DECLINE IN COGNITIVE FUNCTION |
|---|---|---|---|---|---|
| 1 | FIRST GROUP | 70 YEARS OF AGE OR MORE, LIVING ALONE, DECLINE IN COGNITIVE FUNCTION | 70 YEARS OF AGE OR MORE | LIVING ALONE | YES |
| 2 | SECOND GROUP | 70 YEARS OF AGE OR MORE, LIVING ALONE, NO DECLINE IN COGNITIVE FUNCTION | 70 YEARS OF AGE OR MORE | LIVING ALONE | NO |
| 3 | THIRD GROUP | UNDER 70 YEARS OF AGE, LIVING ALONE, DECLINE IN COGNITIVE FUNCTION | UNDER 70 YEARS OF AGE | LIVING ALONE | YES |
| ... | ... | ... | ... | ... | ... |

| No. | SUPPORT CONTENT | FIRST GROUP | SECOND GROUP | THIRD GROUP | ... |
|---|---|---|---|---|---|
| 1 | SUPPORT TO INTAKE WATER DAILY | ● | ● | ● | ... |
| 2 | SUPPORT TO TAKE NUTRITION FROM MEALS | ● | | ● | ... |
| 3 | SUPPORT TO KEEP A HYGIENIC STATE IN ORAL CAVITY | ○ | ○ | ● | ... |
| 4 | SUPPORT TO MANAGE AND TAKE SUBSCRIBED MEDICINES | | ○ | ○ | ... |
| ... | ... | ... | ... | ... | ... |

| No. | SUPPORT CONTENT | FIRST GROUP | SECOND GROUP | THIRD GROUP | ... |
|---|---|---|---|---|---|
| 1 | ORGANIZE SUPPORT SYSTEM TO URGE UNDERSTANDING OF DISEASE | | | | |
| 2 | ORGANIZE SUPPORT SYSTEM TO REGULARLY VISIT DOCTOR | ● | ● | ● | |
| 3 | ORGANIZE SUPPORT TO BE ABLE TO COMPREHEND STATE DIFFERENT FROM USUAL ONE | ○ | ○ | ○ | |
| 4 | ORGANIZE SUPPORT TO BE ABLE TO CONFIRM TARGET BLOOD PRESSURE | | | | |
| ... | | ... | ... | ... | |

FIG.5

| No. | CURRENT STATE | FUTURE STATE | SCORE |
|---|---|---|---|
| 1 | SELF-SUPPORT/NEARLY SELF-SUPPORT NOT HINDERED/NOT APPLICABLE | POSSIBILITY OF SELF-SUPPORT POSSIBLE OF IMPROVEMENT | LOW |
| 2 | FULL SUPPORT HINDERED | NO POSSIBILITY OF SELF-SUPPORT NO POSSIBILITY OF IMPROVEMENT | LOW |
| 3 | FULL SUPPORT HINDERED | POSSIBILITY OF SELF-SUPPORT POSSIBLE OF IMPROVEMENT | MIDDLE |
| 4 | NO INFORMATION/UNEVALUABLE | NO INFORMATION/UNEVALUABLE | HIGH |
| ... | ... | ... | ... |

133

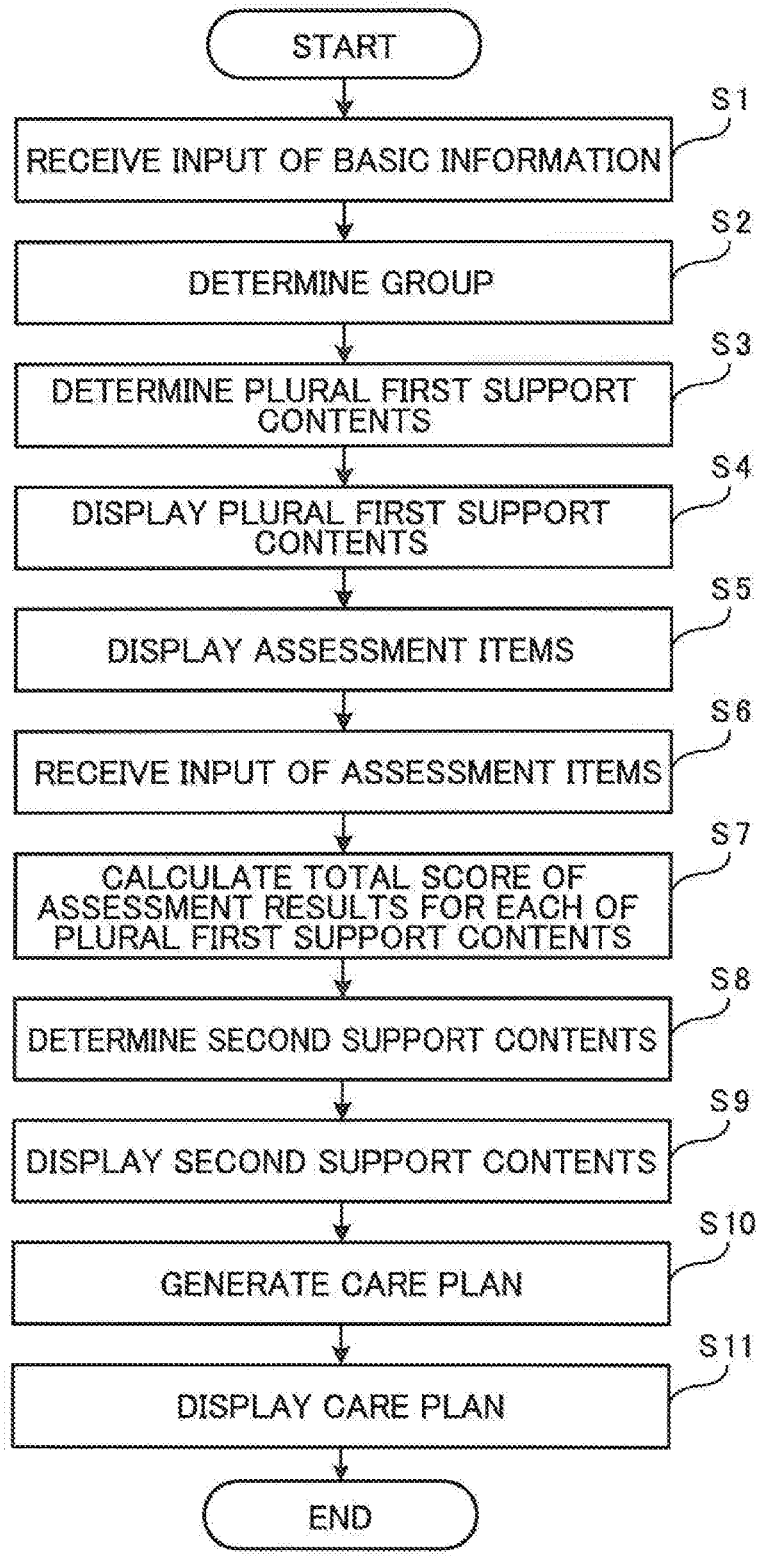

FIG.7

PROFILE
- NAME
- SEX  ● MALE ○ FEMALE
- AGE
- BIRTHDATE ☐ / ☐ / ☐
- LIVING AREA
- LIVING FORM
- CARE DEGREE
- DECLINE IN COGNITIVE FUNCTION ○ YES ○ NO
- SERVICE USE EXPERIENCE ○ YES ○ NO

DISEASE (SELECT)
● VASCULAR BRAIN DISEASE
○ FEMORAL NECK FRACTURE
○ HEART FAILURE
○ KIDNEY FAILURE
...

FREE DESCRIPTION
REMARKS, ETC.

⊙ SUPPORT TO INTAKE WATER DAILY — 143, 1431

1. · UNDERSTANDING OF NECESSARY WATER CONTENT [CONDITION] — 1432

① CURRENT STATE : ○ NOT HINDERED/NOT APPLICABLE ○ PARTIALLY HINDERED ◉ HINDERED ○ NO INFORMATION/EVALUABLE

② FUTURE STATE : ◉ POSSIBILITY OF IMPROVEMENT ○ NO POSSIBILITY OF IMPROVEMENT ○ NO INFORMATION/EVALUABLE

2. PREPARATION OF NECESSARY WATER [CONDITION]

① CURRENT STATE : ○ NOT HINDERED/NOT APPLICABLE ○ PARTIALLY HINDERED ○ HINDERED ○ NO INFORMATION/EVALUABLE

② FUTURE STATE : ○ POSSIBILITY OF IMPROVEMENT ○ NO POSSIBILITY OF IMPROVEMENT ○ NO INFORMATION/EVALUABLE 1433, 1434

INFORMATION PROCESSING METHOD, INFORMATION PROCESSING APPARATUS AND NON-TRANSITORY COMPUTER-READABLE RECORDING MEDIUM STORING INFORMATION PROCESSING PROGRAM

FIELD OF THE INVENTION

The present disclosure relates to an information processing method and an information processing apparatus for outputting presentation information for presenting a support content for a care recipient or assistance recipient to a user, and a non-transitory computer-readable recording medium storing an information processing program.

BACKGROUND ART

In recent years, care management has been utilized by substantially all care service users in the care insurance system. The care management has been introduced as a mechanism for ensuring the integrated provision of a care service corresponding to user's mental and physical conditions and the choice of a service by the user him/herself at the field level.

Care managers are assigned as people in charge of care management in the care insurance system in in-home care support facilities, community general support centers, care insurance facilities and the like. Duties of a care manager are mainly performed as follows.

First of all, the care manager interviews a care recipient or assistance recipient and assesses the state of the care recipient or assistance recipient. Subsequently, the care manager prepares a draft of a care plan. Then, services based on the care plan are provided to the care recipient or assistance recipient. Thereafter, the care manager monitors the care recipient or assistance recipient and changes the care plan if necessary.

Conventionally, the determination of assessment items, an assessment method and support contents depend on the care manager's experience or performance. Thus, a particularly inexperienced care manager is not necessarily capable of preparing a care plan suitable for a care recipient or assistance recipient.

In such a situation, it is required to prepare a suitable care plan corresponding to a state of each insured person and perform maintenance regardless of the experience and ability of a care manager who prepares the care plan.

Accordingly, for example, a care plan preparation support system of Japanese Unexamined Patent Publication No. 2002-304470 prepares an in-home service plan document, which is a document compiling the entire care plan of each insured person, service utilization slips and service providing slips for each insured person based on common item data and additional information of each insured person, a selected problem to be solved, a target in nursing care and the contents of care services, which are input by a user.

However, with the above conventional technique, support contents suitable for a care recipient or assistance recipient may not be presented and further improvement has been necessary.

SUMMARY OF THE INVENTION

The present disclosure has been made to solve the above problem and aims to provide an information processing method and an information processing apparatus capable of selecting and presenting a support content more suitable for a care recipient or assistance recipient and a non-transitory computer-readable recording medium storing an information processing program.

An information processing method according to one aspect of the present disclosure is performed by a computer and includes determining a plurality of first support contents corresponding to a care recipient or assistance recipient from a plurality of support contents based on basic information on the care recipient or assistance recipient, outputting first presentation information for presenting the plurality of first support contents and assessment items respectively associated with the plurality of first support contents to a user, determining a second support content from the plurality of first support contents based on assessment results input by the user for the assessment items, and outputting second presentation information for presenting the second support content to the user.

BRIEF DESCRIPTION OF THE DRAWINGS

FIG. 2 is a diagram showing an example of a table stored in a basic group database in the first embodiment, FIG. 3 is a diagram showing an example of a basic support content table stored in a support content database in the first embodiment, FIG. 4 is a diagram showing an example of a disease-based support content table stored in the support content database in the first embodiment, FIG. 5 is a diagram showing an example of a table stored in a score database in the first embodiment, FIG. 6 is a flow chart showing a care management support process in the care management support apparatus according to the first embodiment of the present disclosure, FIG. 7 is a diagram showing an example of a basic information input screen for inputting basic information in the first embodiment, FIG. 9 is a diagram showing an example of an assessment item display screen for displaying assessment items and receiving the input of assessment results for the assessment items in the first embodiment.

Figure 1:
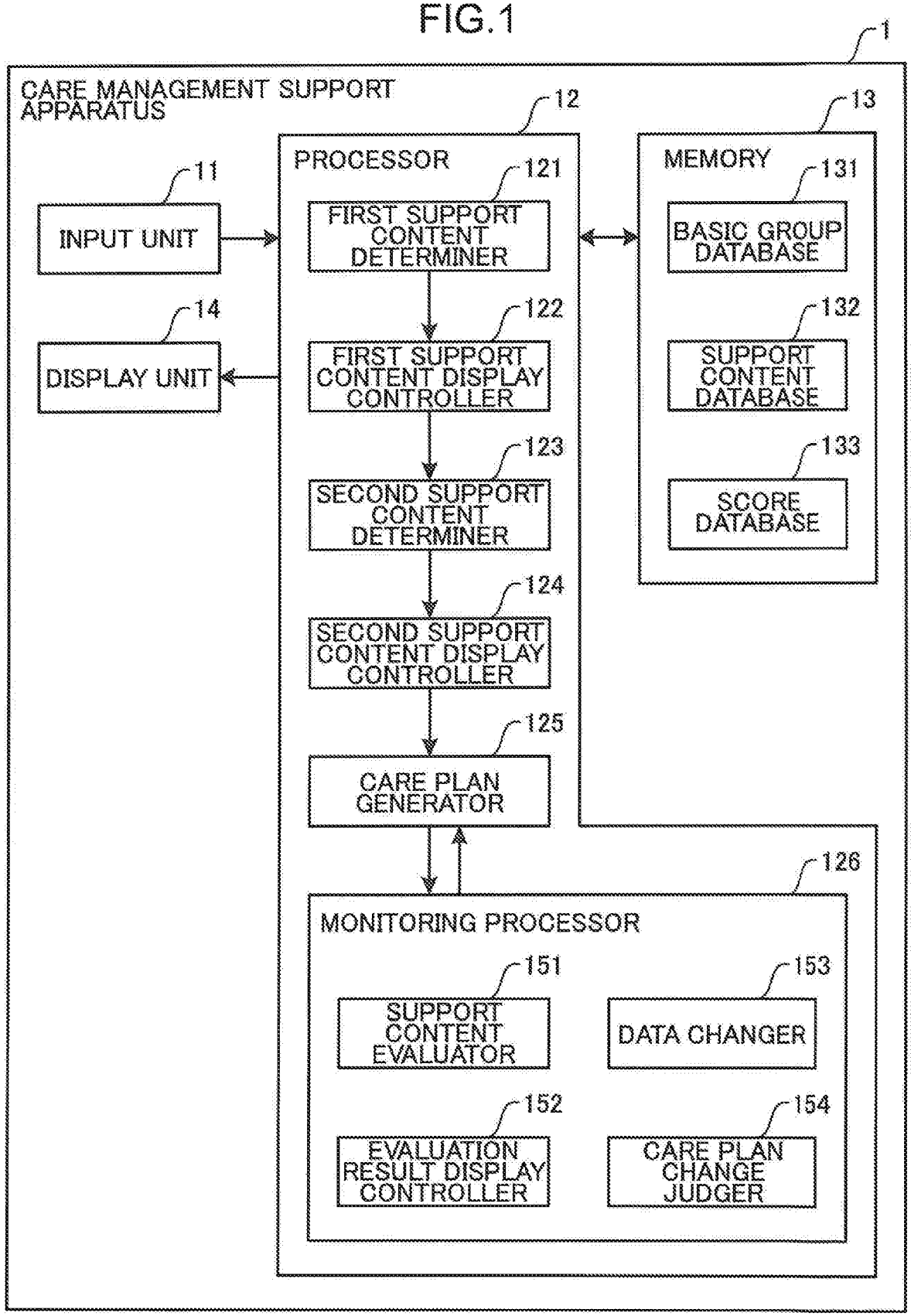
FIG. 1 is a block diagram showing the configuration of a care management support apparatus in a first embodiment of the present disclosure.

DESCRIPTION OF EMBODIMENTS (Knowledge Serving as Basis for Present Disclosure)

For example, in the care plan preparation support system of Japanese Unexamined Patent Publication No. 2002-304470, data on assessment items (assessment data) for task analysis obtained by visiting and surveying each insured person is first input on an assessment input screen by a care manager in charge of each insured person. Then, based on the input assessment data of each insured person, areas having a possibility of becoming problematic and a group of problems to be solved are extracted for each insured person, and a warning is displayed for the areas having a possibility of becoming problematic and the group of problems to be solved on an area review screen. After the areas and the group of problems to be solved, which were warned and displayed on the area review screen, are studied in detail by the care manager, additional assessment data on the warned and displayed areas and group of problems to be solved is selected and input to determine specific problems to be solved for each insured person. Problems to be solved, which might possibly become problematic and are matching the insured person's condition, are extracted from master data for the problems to be solved. If one or more problems to be solved having a possibility of becoming problematic are extracted, an optimal problem to be solved viewed from the insured person's individual situation is determined by the care manager.

With the above conventional technique, how problems to be solved having a possibility of becoming problematic are extracted is not disclosed and appropriate problems to be solved may not be extracted.

Further, there are a large number of assessment items and the contents of the assessment items are also in a wide range. Thus, an operation of assessing all the items by the care manager is a time intensive operation in the care field suffering from a labor shortage.

To solve the above problem, the information processing method according to one aspect of the present disclosure is performed by a computer and includes determining a plurality of first support contents corresponding to a care recipient or assistance recipient from a plurality of support contents based on basic information on the care recipient or assistance recipient, outputting first presentation information for presenting the plurality of first support contents and assessment items respectively associated with the plurality of first support contents to a user, determining a second support content from the plurality of first support contents based on assessment results input by the user for the assessment items, and outputting second presentation information for presenting the second support content to the user.

According to this configuration, the plurality of first support contents corresponding to the care recipient or assistance recipient are determined from the plurality of support contents based on the basic information on the care recipient or assistance recipient. Subsequently, the second support content is determined from the plurality of first support contents based on the assessment results input by the user for the assessment items respectively associated with the plurality of first support contents.

Thus, the screening of the support contents based on the basic information on the care recipient or assistance recipient and the screening of the support contents based on the assessment results input by the user for the assessment items are performed in two stages. Therefore, the support content more suitable for the care recipient or assistance recipient can be selected and presented.

Further, in the above information processing method, the assessment result may include a current state of the care recipient or assistance recipient and a future state of the care recipient or assistance recipient.

According to this configuration, since the assessment result includes not only the current state of the care recipient or assistance recipient, but also the future state of the care recipient or assistance recipient, the second support content taking into account the future self-support of the care recipient or assistance recipient can be determined.

Further, in the above information processing method, the assessment results may be converted into numerical values and the second support content may be determined from the plurality of first support contents based on the numerical values, and a numerical value when the current state is not assessable by the user and a numerical value when the future state is not assessable by the user may be higher than a numerical value when the current state is assessable by the user and a numerical value when the future state is assessable by the user.

According to this configuration, the assessment results are converted into the numerical values and the second support content is determined from the plurality of first support contents based on the numerical values. The numerical value when the current state is not assessable by the user and the numerical value when the future state is not assessable by the user are higher than the numerical value when the current state is assessable by the user and the numerical value when the future state is assessable by the user.

Thus, the second support content corresponding to the assessment item for which the current state is not assessable by the user and the assessment item for which the future state is not assessable by the user can be determined with priority, and the support content with insufficient information can be presented to the user with priority.

Further, in the above information processing method, the assessment results may be converted into numerical values and the second support content may be determined from the plurality of first support contents based on the numerical values.

According to this configuration, the assessment results are converted into the numerical values and the second support content is determined from the plurality of first support contents based on the numerical values. Thus, the first support contents can be extracted in the decreasing order of the numerical values of the assessment results from the plurality of first support contents by giving high numerical values to the assessment results having high degrees of importance, and the extracted first support contents can be determined as the second support contents.

Further, the above information processing method may include outputting third presentation information for presenting the second support content and the assessment item associated with the second support content to the user after a service based on a care plan generated based on the second support content is performed for the care recipient or assistance recipient, evaluating the second support content based on an assessment result input by the user for the assessment item, and outputting fourth presentation information for presenting an evaluation result of the second support content to the user.

According to this configuration, the second support content and the assessment item associated with the second support content are presented to the user after the service based on the care plan generated based on the second support content is performed for the care recipient or assistance recipient, and the second support content is evaluated based on the assessment result input by the user for the assessment item.

Accordingly, the second support content is evaluated based on the assessment result input by the user for the assessment item associated with the second support content. Therefore, the user can monitor the care plan generated based on the second support content by confirming the evaluation result of the second support content.

Further, the above information processing method may further include changing a presentation order of the second support content based on the evaluation result.

According to this configuration, the presentation order of the second support content is changed based on the evaluation result. Thus, if a degree of importance of the second support content changes, for example, as a result of performing the service based on the care plan generated based on the second support content for the care recipient or assistance recipient, the presentation order of the second support content can be changed according to the changed degree of importance and the second support content having a higher degree of importance can be presented with priority.

Further, the above information processing method may further include judging whether or not to change the care plan based on the evaluation result and the care plan.

According to this configuration, whether or not to change the care plan is judged based on the evaluation result and the care plan. Thus, for example, if the service corresponding to the second support content of the care plan contributed to an improvement in the state of the care recipient or assistance recipient, this service corresponding to the second support content can be continued or stopped or changed to another service.

Further, in the above information processing method, when the care plan is stopped or changed, the stopped or changed care plan and the past care plan may be compared and a ground for a part changed from the past care plan may be presented. Particularly, it is desirable to present a ground for a deleted support content. This makes it easier to obtain the consent of the care recipient or assistance recipient or his/her family or the like.

Further, in the above information processing method, the service corresponding to the care plan may be stopped if the assessment item being monitored improved after the elapse of a predetermined period, and the service corresponding to the care plan may be changed if the assessment item being monitored worsened after the elapse of a predetermined period. In this way, judgment criteria as to whether or not to stop the service corresponding to the care plan may be set.

Further, the above information processing method may further include obtaining sensor information, analyzing the sensor information, and outputting third presentation information for presenting an analysis result of the sensor information to the user together with the support content and the assessment item associated with the second support content.

According to this configuration, since the analysis result of the obtained sensor information is presented to the user together with the second support content and the assessment item associated with the support content, the user can more precisely input an answer for the assessment item by confirming the analysis result of the sensor information.

Further, the above information processing method may further include outputting fifth presentation information for presenting a sensor for obtaining the sensor information to the user based on at least one of the basic information and the assessment result.

According to this configuration, since the sensor for obtaining the sensor information is presented to the user based on at least one of the basic information and the assessment result, the sensor corresponding to the state of the care recipient or assistance recipient can be presented to the user.

An information processing apparatus according to another aspect of the present disclosure includes a first determiner for determining a plurality of first support contents corresponding to a care recipient or assistance recipient from a plurality of support contents based on basic information on the care recipient or assistance recipient, a first output unit for outputting first presentation information for presenting the plurality of first support contents and assessment items respectively associated with the plurality of first support contents to a user, a second determiner for determining a second support content from the plurality of first support contents based on assessment results input by the user for the assessment items, and a second output unit for outputting second presentation information for presenting the second support content to the user.

According to this configuration, the plurality of first support contents corresponding to the care recipient or assistance recipient are determined from the plurality of support contents based on the basic information on the care recipient or assistance recipient. Subsequently, the second support content is determined from the plurality of first support contents based on the assessment results input by the user for the assessment items respectively associated with the plurality of first support contents.

Thus, the screening of the support contents based on the basic information on the care recipient or assistance recipient and the screening of the support contents based on the assessment results input by the user for the assessment items are performed in two stages. Therefore, the support content more suitable for the care recipient or assistance recipient can be selected and presented.

A non-transitory computer-readable recording medium storing an information processing program according to another aspect of the present disclosure causes a computer to determine a plurality of first support contents corresponding to a care recipient or assistance recipient from a plurality of support contents based on basic information on the care recipient or assistance recipient, output first presentation information for presenting the plurality of first support contents and assessment items respectively associated with the plurality of first support contents to a user, determine a second support content from the plurality of first support contents based on assessment results input by the user for the assessment items, and output second presentation information for presenting the second support content to the user.

According to this configuration, the plurality of first support contents corresponding to the care recipient or assistance recipient are determined from the plurality of support contents based on the basic information on the care recipient or assistance recipient. Subsequently, the second support content is determined from the plurality of first support contents based on the assessment results input by the user for the assessment items respectively associated with the plurality of first support contents.

Thus, the screening of the support contents based on the basic information on the care recipient or assistance recipient and the screening of the support contents based on the assessment results input by the user for the assessment items are performed in two stages. Therefore, the support content more suitable for the care recipient or assistance recipient can be selected and presented.

Hereinafter, embodiments of the present disclosure are described with reference to the accompanying drawings. Note that the following embodiments are specific examples of the present disclosure and do not limit the technical scope of the present disclosure.

First Embodiment

FIG. 1 is a block diagram showing the configuration of a care management support apparatus in a first embodiment of the present disclosure. A care management support apparatus 1 is, for example, a personal computer or tablet computer. The care management support apparatus 1 includes an input unit 11, a processor 12, a memory 13 and a display unit 14.

The input unit 11 is, for example, a mouse, keyboard, touch panel or the like and receives an input operation of a user. The user in this embodiment is, for example, a care manager.

The input unit 11 receives the input of basic information on a care recipient or assistance recipient by the user. The basic information includes, for example, the name, age, living status, the presence or absence of decline in cognitive function, and disease information of the care recipient or assistance recipient. The living status indicates whether or not the care recipient or assistance recipient is living alone. The disease information indicates disease(s) from which the care recipient or assistance recipient is currently suffering and/or disease(s) from which the care recipient or assistance recipient suffered in the past.

Note that the disease in the first embodiment indicates, for example, a causative disease because of which the care recipient came to need care or because of which the assistance recipient came to need assistance. Examples of the disease include a vascular brain disease ranked top of the causative diseases in the certification of needed long-term care, and a femoral neck fracture having a high possibility of improvement by providing suitable supports. Note that the disease information is not limited to the above vascular brain disease and femoral neck fracture and may be another disease such as a heart failure or kidney failure.

Further, the basic information is not limited to the above and may include other pieces of information such as insured person information on a long-term care insurance of the care recipient and the like and care power information representing the presence or absence of a caregiver.

The display unit 14 is, for example, a liquid crystal display device and displays various pieces of information.

The memory 13 is implemented by an auxiliary storage device such as a HDD (hard disk drive), RAM (random access memory) or semiconductor memory. The memory 13 includes a basic group database 131, a support content database 132 and a score database 133.

The processor 12 includes a first support content determiner 121, a first support content display controller 122, a second support content determiner 123, a second support content display controller 124, a care plan generator 125 and a monitoring processor 126.

The basic group database 131 stores a table associating a plurality of groups and conditions for belonging to each group.

FIG. 2 is a diagram showing an example of the table stored in the basic group database in the first embodiment. As shown in FIG. 2, the basic group database 131 stores a table associating a plurality of groups with the age, living status and decline in cognitive function.

For example, a care recipient or assistance recipient who is 70 years of age or more and living alone and whose cognitive function has declined is classified into a first group. Further, a care recipient or assistance recipient who is 70 years of age or more and living alone and whose cognitive function has not declined is classified into a second group.

Note that the basic group database 131 may further associate other pieces of information such as the care power information representing the presence or absence of a caregiver with the plurality of groups.

The support content database 132 stores a table associating a plurality of support contents and degrees of importance of the plurality of groups corresponding to the plurality of support contents. The plurality of support contents include basic support contents common to the aged in general based on functions and physiology of the aged, and disease-based support contents different for each disease.

FIG. 3 is a diagram showing an example of a basic support content table stored in the support content database in the first embodiment. FIG. 4 is a diagram showing an example of disease-based support content tables stored in the support content database in the first embodiment. In the first embodiment, the degrees of importance of the plurality of groups are classified into three stages. Black circles in FIGS. 3 and 4 indicate a highest degree of importance, white circles indicate a second highest degree of importance, and blanks indicate a lowest degree of importance.

Note that the classification stages of the degrees of importance are not limited to three and may be other than three. The degrees of importance may be classified into more than three stages and a display method on the display unit 14 may be changed according to the degree of importance.

In a basic support content table 1321 shown in FIG. 3, the basic support contents and the degree of importance of the plurality of groups are associated. In a disease-based support content table 1322 shown in FIG. 4, disease-based support contents corresponding to the vascular brain disease and the degrees of importance of the plurality of groups are associated. Further, in a disease-based support content table 1323 shown in FIG. 4, disease-based support contents corresponding to the femoral neck fracture and the degrees of importance of the plurality of groups are associated.

For example, if the basic support content is a "support to intake water daily" in FIG. 3, the highest degree of importance is set for the first, second and third groups. Further, if the disease-based support content corresponding to the vascular brain disease is "organize a support system to urge the understanding of disease" in FIG. 4, the lowest degree of importance is set for the first, second and third groups.

Note that the support content database 132 stores assessment items respectively associated with the plurality of support contents. Further, the support content database 132 stores the need of each of the plurality of support contents and information on specific implementation methods.

The first support content determiner 121 determines a plurality of first support contents corresponding to the care recipient or assistance recipient from the plurality of support contents based on the basic information on the care recipient or assistance recipient. The first support content determiner 121 refers to the basic group database 131 and classifies the care recipient or assistance recipient into any one of the plurality of groups based on the basic information on the care recipient or assistance recipient. Then, the first support content determiner 121 refers to the support content database 132 and determines a plurality of first support contents having a high degree of importance and corresponding to the classified group from the plurality of support contents.

The first support content display controller 122 outputs first presentation information for presenting the plurality of first support contents and the assessment items respectively associated with the plurality of first support contents to the user. The first support content display controller 122 outputs the first presentation information to the display unit 14. The assessment item indicates an item to be confirmed with the care recipient or assistance recipient for the first support content.

The display unit 14 displays the plurality of first support contents and the assessment items respectively associated with the plurality of first support contents when the first presentation information is input from the first support content display controller 122.

The input unit 11 receives the input by the user for the assessment items associated with the plurality of first support contents displayed on the display unit 14. The user confirms with the care recipient or assistance recipient for each of the assessment items and inputs a confirmation result in the input unit 11. Note that the user's input is essentially required for the assessment items associated with the first support contents having the highest degree of importance, whereas the user's input may be arbitrary for the assessment items associated with the first support contents having the second highest degree of importance.

The score database 133 stores a table associating the user's answers for the assessment items (assessment results) and scores.

FIG. 5 is a diagram showing an example of a table stored in the score database in the first embodiment.

The assessment result includes the current state of the care recipient or assistance recipient and the future state of the care recipient or assistance recipient. Specifically, the input unit 11 receives the input of the current state of the care recipient or assistance recipient and the future state of the care recipient or assistance recipient for the assessment items.

The score database 133 shown in FIG. 5 stores a table associating combinations of the current state and the future state and scores. For example, if the current state is "hindered" and the future state is "no possibility of improvement" in FIG. 5, a low score is associated. For example, if the current state is "hindered" and the future state is "possibility of improvement", a middle score between the low score and a high score is associated.

Note that although three stages of score including the low, middle and high scores are associated with the combinations of the current state and the future state of the care recipient or assistance recipient in the score database 133 in the first embodiment, the present disclosure is not particularly limited to this and four or more stages of score may be associated.

In the first embodiment, a higher score is set for the assessment result requiring support and the assessment result having no possibility of improvement than for the assessment result requiring no support and the assessment result having a possibility of improvement.

Note that a score (numerical value) when the user cannot assess the current state and a score (numerical value) when the user cannot assess the future state are higher than a score (numerical value) when the user can assess the current state and a score (numerical value) when the user can assess the future state. Specifically, for example, if the current state is "no information/unevaluable" and the future state is "no information/unevaluable" in FIG. 5, the high score is associated. For the support content for which no assessment result is obtained, whether or not the support content is necessary in the future can be judged again by monitoring in addition to the care plan.

Further, the score database 133 may store a table associating each of the current state and the future state and the score. Further, the score database 133 may store a table associating scores different for each assessment item with the assessment results.

Further, either the current state or the future state may be displayed/user input for each assessment item.

Further, the input of the assessment items by the user may be an automatic input by another system or at the time of the last assessment.

Further, if the input of a plurality of the same assessments is necessary, contents at the time of initial input may be automatically input.

The second support content determiner 123 determines second support contents from the plurality of first support contents based on the assessment results input by the user for the assessment items. The second support content determiner 123 converts the assessment results into numerical values and determines the second support contents from the plurality of first support contents based on the numerical values. Specifically, the second support content determiner 123 refers to the score database 133, totals the scores of the assessment results for each of the plurality of first support contents and calculates a total score for each of the plurality of first support contents. The support content having a higher total score can be said to be a more important support content requiring future monitoring. The second support content determiner 123 determines a predetermined number of the second support contents in the decreasing order of the total scores from the plurality of first support contents. For example, the second support content determiner 123 determines top ten second support contents in the total score from the plurality of first support contents.

Further, the second support content determiner 123 may determine the second support contents having the total scores equal to or larger than a threshold value from the plurality of first support contents.

The second support content display controller 124 outputs second presentation information for presenting the second support contents to the user. The second support content display controller 124 outputs the second presentation information to the display unit 14.

The display unit 14 displays the second support contents when the second presentation information is input from the second support content display controller 124.

The care plan generator 125 automatically generates a care plan for the care recipient or assistance recipient based on the second support contents determined by the second support content determiner 123. Note that the care plan shows the types, contents and use frequencies and times of services associated with the second support contents.

Note that although the care plan generator 125 automatically generates the care plan in the first embodiment, the present disclosure is not particularly limited to this. The input unit 11 may receive the generation of a care plan by the user based on the second support contents displayed on the display unit 14. Further, the input unit 11 may receive the user's revision for the care plan automatically generated by the care plan generator 125.

The monitoring processor 126 includes a support content evaluator 151, an evaluation result display controller 152, a data changer 153 and a care plan change judger 154.

The support content evaluator 151 outputs third presentation information for presenting the second support contents and the assessment items associated with the second support contents to the user after the services based on the care plan generated based on the second support contents are performed for the care recipient or assistance recipient. The support content evaluator 151 outputs the third presentation information to the display unit 14.

The display unit 14 displays the second support contents and the assessment items associated with the second support contents when the third presentation information is input from the support content evaluator 151. The input unit 11 receives the input by the user for the assessment items associated with the second support contents displayed on the display unit 14.

Further, the support content evaluator 151 evaluates the second support contents based on the assessment results input by the user for the assessment items. The support content evaluator 151 converts the assessment results into numerical values and evaluates the second support contents based on the numerical values. Specifically, the support content evaluator 151 refers to the score database 133, totals the scores of the assessment results of the second support contents and calculates the total scores of the second support contents as evaluation results.

The evaluation result display controller 152 outputs fourth presentation information for presenting the evaluation results of the second support contents to the user. Here, the evaluation results of the second support contents are the total scores of the assessment results of the second support contents. The evaluation result display controller 152 outputs the fourth presentation information to the display unit 14.

The display unit 14 displays the evaluation results of the second support contents when the fourth presentation information is input from the evaluation result display controller 152.

The data changer 153 changes the presentation order of the second support content based on the evaluation result. Specifically, the data changer 153 changes the score in the score database 133 corresponding to the assessment result to be higher than the current score for the second support contact including the assessment result of "possibility of improvement" and having a lower total score of the evaluation result than the other second support contents. In this way, the total score of the second support content including the assessment result of "possibility of improvement" and having a lower total score of the evaluation result than the other second support contents increases and the presentation order of this second support content is changed to a higher rank.

The care plan change judger 154 judges whether or not to change the care plan based on the evaluation results and the care plan. Specifically, if the state of the care recipient or assistance recipient was improved by performing the services corresponding to the care plan, the total scores of the second support contents after the services corresponding to the care plan were performed are lower than the total scores of the support contents before the services corresponding to the care plan were performed. In this case, the services corresponding to the second support contents of the care plan can be stopped or changed to other services, assuming that the services corresponding to the care plan contributed to an improvement in the state of the care recipient or assistance recipient. Accordingly, the care plan change judger 154 judges to change the current service contents of the care plan if the total scores of the second support contents after the services corresponding to the care plan were performed became lower than the total scores of the support contents before the services corresponding to the care plan were performed. Note that the memory 13 preferably stores the total scores of the support contents before the services corresponding to the care plan were performed.

Further, if the services corresponding to the second support contents of the care plan contribute to an improvement in the state of the care recipient or assistance recipient, these services corresponding to the second support contents can also be continued. In this case, the care plan change judger 154 may judge not to change the current service contents of the care plan if the total scores of the second support contents after the services corresponding to the care plan were performed became lower than the total scores of the second support contents before the services corresponding to the care plan were performed.

Further, if the state of the care recipient or assistance recipient worsened by performing the services corresponding to the care plan, the total scores of the second support contents after the services corresponding to the care plan were performed become higher than the total scores of the second support contents before the services corresponding to the care plan were performed. In this case, the services corresponding to the second support contents of the care plan can be stopped or changed to other services, assuming that the services corresponding to the second support contents of the care plan do not contribute to an improvement in the state of the care recipient or assistance recipient. Accordingly, the care plan change judger 154 may judge to change the current service contents of the care plan also if the total scores of the second support contents after the services corresponding to the care plan were performed became higher than the total scores of the support contents before the services corresponding to the care plan were performed.

Further, the memory 13 may further include a care plan database storing care plans generated in the past by the care plan generator 125 and a support need database storing information representing reasons why a support content is necessary if the support content is added and information representing reasons why a support content is unnecessary if the support content is deleted.

In this case, the care plan generator 125 may compare the generated care plan with the past care plan stored in the care plan database. The care plan generator 125 may present grounds for a part changed from the past care plan. Specifically, if a new support content is added to the generated care plan, the care plan generator 125 may read information stored in the support need database and representing reasons why the new support content is necessary and display the information representing the reasons why the new support content is necessary on the display unit 14. Further, if the past support content was deleted from the generated care plan, the care plan generator 125 may read information stored in the support need database and representing reasons why the deleted support content is unnecessary and display the information representing the reasons why the deleted support content is unnecessary on the display unit 14.

Further, the data changer 153 may compare the stopped or changed care plan and the past care plan stored in the care plan database if the care plan was stopped or changed. The data changer 153 may present grounds for a part changed from the past care plan. Specifically, if a new support content is added to the stopped or changed care plan, the data changer 153 may read information stored in the support need database and representing reasons why the new support content is necessary and display the information representing the reasons why the new support content is necessary on the display unit 14. Further, if the past support content is deleted from the stopped or changed care plan, the data changer 153 may read information stored in the support need database and representing reasons why the deleted support content is unnecessary and display the reasons why the deleted support content is unnecessary on the display unit 14.

By presenting the reasons why the support content was added or why the support content was deleted in this way, the consent of the care recipient, assistance recipient, his/her family or the like is more easily obtained.

Further, the care plan change judger 154 may stop the services corresponding to the care plan if the assessment items being monitored improved after the elapse of a predetermined period. The predetermined period is, for example, three months. Further, the care plan change judger 154 may change the services corresponding to the care plan if the assessment items being monitored worsened after the elapse of the predetermined period. As just described, judgment criteria as to whether or not to stop the services corresponding to the care plan may be set.

Note that the care management support apparatus 1 may be a server. If the care management support apparatus 1 is a server, the care management support apparatus 1 may not include the input unit 11 and the display unit 14 and a user terminal communicably connected to the care management support apparatus 1 via a network may include the input unit 11 and the display unit 14. The user terminal is, for example, a smartphone, tablet computer or personal computer and may transmit the basic information and the assessment result information to the care management support apparatus 1 and receive the first, second, third and fourth presentation information from the care management support apparatus 1. Then, the user terminal may generate each display screen from the received first, second, third and fourth presentation information and display the generated display screens.

Next, a care management support process in the care management support apparatus 1 according to the first embodiment of the present disclosure is described.

FIG. 6 is a flow chart showing the care management support process in the care management support apparatus according to the first embodiment of the present disclosure.

First, in Step S1, the input unit 11 receives the input of the basic information on the care recipient or assistance recipient by the user. The input unit 11 outputs the input basic information to the first support content determiner 121.

FIG. 7 is a diagram showing an example of a basic information input screen for inputting the basic information in the first embodiment. The display unit 14 displays a basic information input screen 141 for inputting the basic information.

The basic information input screen 141 shown in FIG. 7 includes a profile input field 1411, a disease input field 1412 and a free description field 1413.

The profile input field 1411 receives the input of the name, sex, age, birthdate, living area, living form, care degree, presence or absence of decline in cognitive function and presence or absence of service use experience of the care recipient or assistance recipient. Note that the living form indicates whether the care recipient or assistance recipient is living alone or living with his/her family. The care degree indicates a degree of care need determined in the certification of needed long-term care or the certification of needed support. An input method of each item of the profile input field 1411 may be a direct input, pull-down menu input or check box input.

The disease input field 1412 receives the input of a causative disease because of which the care recipient came to need care or a causative disease because of which the assistance recipient came to need assistance. An input method for the disease input field 1412 may be a check box input. The user selects a disease corresponding to the causative disease from a plurality of diseases such as vascular brain disease, femoral neck fracture, heart failure and kidney failure.

The free description field 1413 receives the input of remarks, etc. An input method for the free description field 1413 may be a direct input.

Note that the basic information on the care recipient or assistance recipient input by the user is not limited to the above.

Referring back to FIG. 6, subsequently in Step S2, the first support content determiner 121 refers to the basic group database 131 and determines a group, to which the care recipient or assistance recipient belongs, from the plurality of groups based on the basic information on the care recipient or assistance recipient.

Subsequently, in Step S3, the first support content determiner 121 refers to the support content database 132 and determines a plurality of first support contents corresponding to the determined group and having a high degree of importance from the plurality of support contents. The first support content display controller 122 outputs the first presentation information for presenting the plurality of first support contents and the assessment items respectively associated with the plurality of first support contents to the user to the display unit 14.

Subsequently, in Step S4, the display unit 14 displays the plurality of first support contents determined by the first support content determiner 121.

Figure 8:
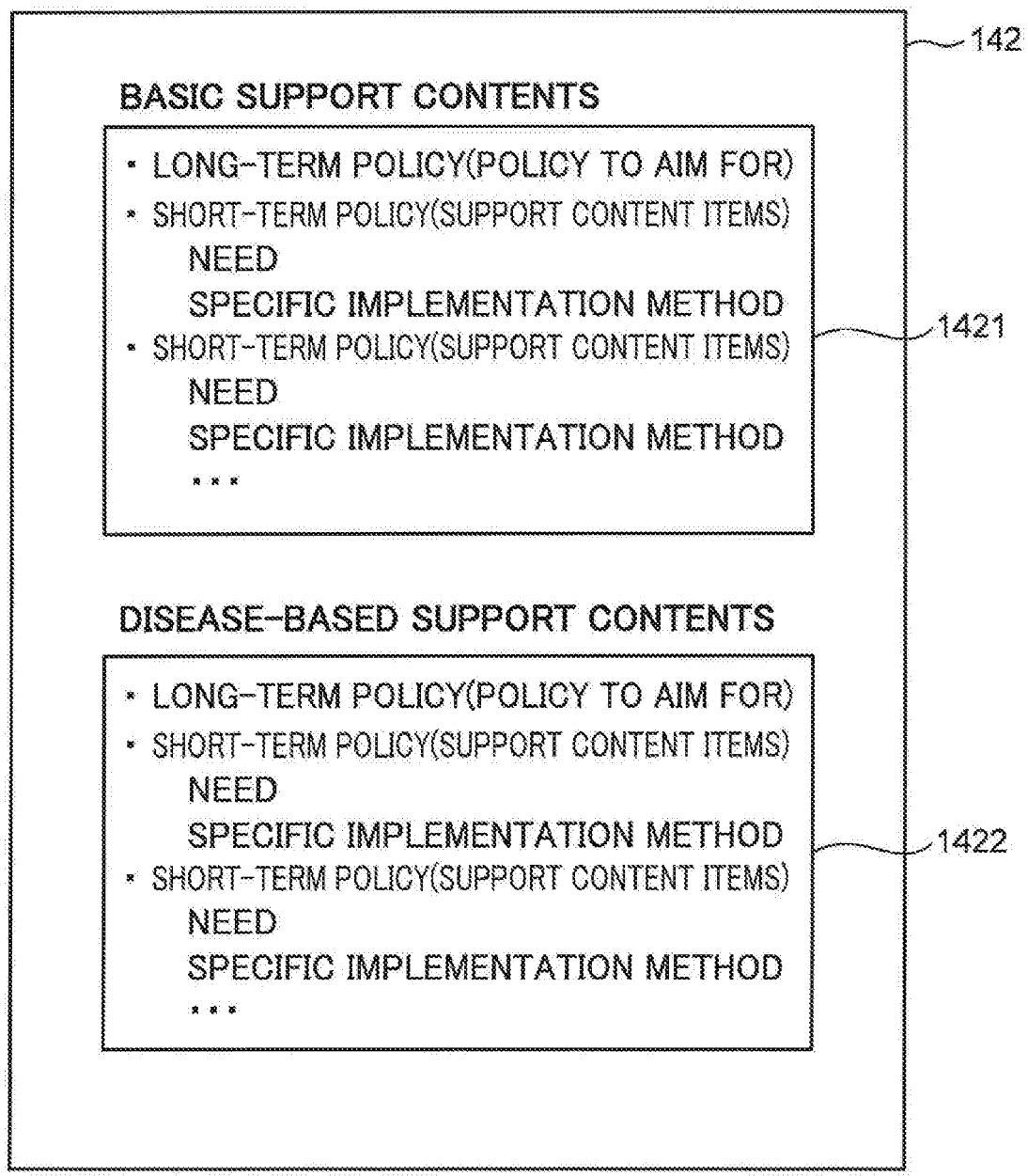
FIG. 8 is a diagram showing an example of a first support content display screen for displaying a plurality of first support contents in the first embodiment.

FIG. 8 is a diagram showing an example of a first support content display screen for displaying the plurality of first support contents in the first embodiment. The display unit 14 displays a first support content display screen 142 for displaying the plurality of first support contents to the user.

The first support content display screen 142 shown in FIG. 8 includes a basic support content display area for presenting basic support contents and a disease-based support content display area 1422 for presenting disease-based support contents.

In the basic support content display area 1421 and the disease-based support content display area 1422, a long-term policy indicates a policy to aim for, and a short-time policy indicates support content items. Further, information representing a need for each support content, information representing a specific implementation method of each support content and the like are displayed in each support content item in association.

Referring back to FIG. 6, subsequently in Step S5, the display unit 14 displays the assessment items respectively associated with the plurality of first support contents determined by the first support content determiner 121.

Subsequently, in Step S6, the input unit 11 receives the input, by the user, of the assessment results for the assessment items displayed on the display unit 14.

FIG. 9 is a diagram showing an example of an assessment item display screen for displaying the assessment items and receiving the input of the assessment results for the assessment items in the first embodiment. The display unit 14 displays an assessment item display screen 143 for presenting the assessment items respectively associated with the plurality of first support contents to the user and receiving the input of the assessment results for the assessment items.

The assessment item display screen 143 includes a support content display area 1431 for displaying the support content, assessment item display areas 1432 for displaying the assessment item, first assessment result input areas 1433 for receiving the input of the current state (condition) of the care recipient or assistance recipient for the assessment item and second assessment result input areas 1434 for receiving the input of the future state (condition) of the care recipient or assistance recipient for the assessment item. An input method for the first assessment result input areas 1433 and the second assessment result input areas 1434 may be a check box input.

The user inputs the current state (condition) of the care recipient or assistance recipient for the assessment item in the first assessment result input area 1433. Further, the user inputs the future state (condition) of the care recipient or assistance recipient for the assessment item in the second assessment result input areas 1434.

Referring back to FIG. 6, subsequently in Step S7, the second support content determiner 123 refers to the score database 133, totals the scores of the assessment results for each of the plurality of first support contents and calculates the total score of the assessment results for each of the plurality of first support contents.

Subsequently, in Step S8, the second support content determiner 123 determines a predetermined number of the second support contents in the decreasing order of the total scores from the plurality of first support contents. The second support content display controller 124 outputs the second presentation information for presenting the second support contents determined by the second support content determiner 123 to the user to the display unit 14. Note that the second support content determiner 123 determines one or more first support contents as one or more second support contents from the plurality of first support contents.

Subsequently, in Step S9, the display unit 14 displays the second support contents determined by the second support content determiner 123.

Figure 10:
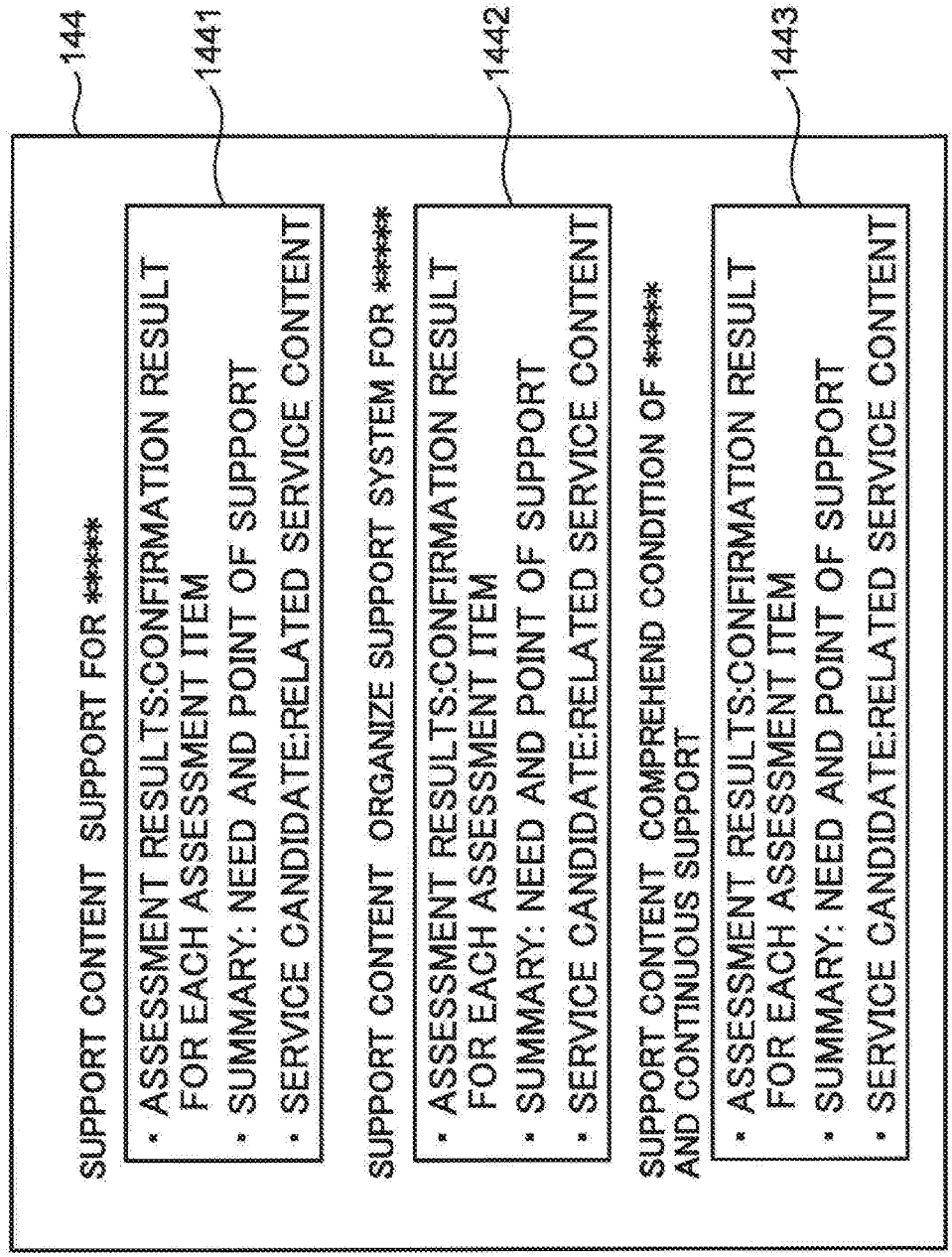
FIG. 10 is a diagram showing an example of a second support content display screen for displaying second support contents in the first embodiment.

FIG. 10 is a diagram showing an example of a second support content display screen for displaying the second support contents in the first embodiment. The display unit 14 displays a second support content display screen 144 for presenting the second support contents to the user.

The predetermined number of the second support contents are displayed in the decreasing order of the total scores of the assessment results on the second support content display screen 144.

The second support content display screen 144 shown in FIG. 10 includes second support content display areas 1441, 1442 and 1443 for presenting the second support contents.

The assessment result indicating a confirmation result for each assessment item, a summary indicating the support need, points and the like and a service candidate indicating a related service content are displayed in the second support content display areas 1441, 1442 and 1443.

Note that the second support content may include items for which information should be collected by a professional. The professional is, for example, a primary care doctor, dentist, nurse, dental hygienist, managerial dietician, caregiver or the like. For example, if the care recipient or assistance recipient has a past medical history of vascular brain disease and a blood pressure self-control is difficult for him/her, the second support content may include an item of monitoring a blood pressure by a nurse.

Further, the memory 13 may further include a professional database storing the support contents, the assessment items and related professionals in association. The second support content display controller 124 may present a professional in charge associated with the assessment item and the second support content together with the second support content. The professional in charge is associated with each profession in advance. Further, the input unit 11 may receive the editing of the assessment items or second support contents by the professional in charge. The second support content display controller 124 may display the assessment items or second support contents edited by the professional in charge on the display unit 14. Further, the input unit 11 may receive the editing of degrees of priority of the assessment items or second support contents by the professional in charge.

Further, the care management support apparatus 1 may include a notifier for notifying the assessment items or second support contents to the professional in charge determined in a conference composed of professionals for determining support policies such as a service staff conference or area care conference. The professional in charge may edit the notified assessment items or second support contents. The notifier may receive the assessment items or second support contents edited by the professional in charge. The second support content display controller 124 may display the assessment items or second support contents edited by the professional in charge on the display unit 14.

Further, the input unit 11 may receive the editing by the professional in charge for the care plan generated by the care plan generator 125. The display unit 14 may display the care plan edited by the professional in charge.

Furthermore, the care plan generator 125 may determine a professional for continuously monitoring each assessment item serving as a monitoring target.

Further, the input unit 11 may receive the input, by the user, of the assessment items to be monitored determined by the service staff conference or area care conference. The input assessment items to be monitored may be stored in the memory 13.

Further, the second support content display controller 124 may output presentation information for presenting the evaluation result of the assessment by the user to the user after the second presentation information is output to the display unit 14.

Figure 11:
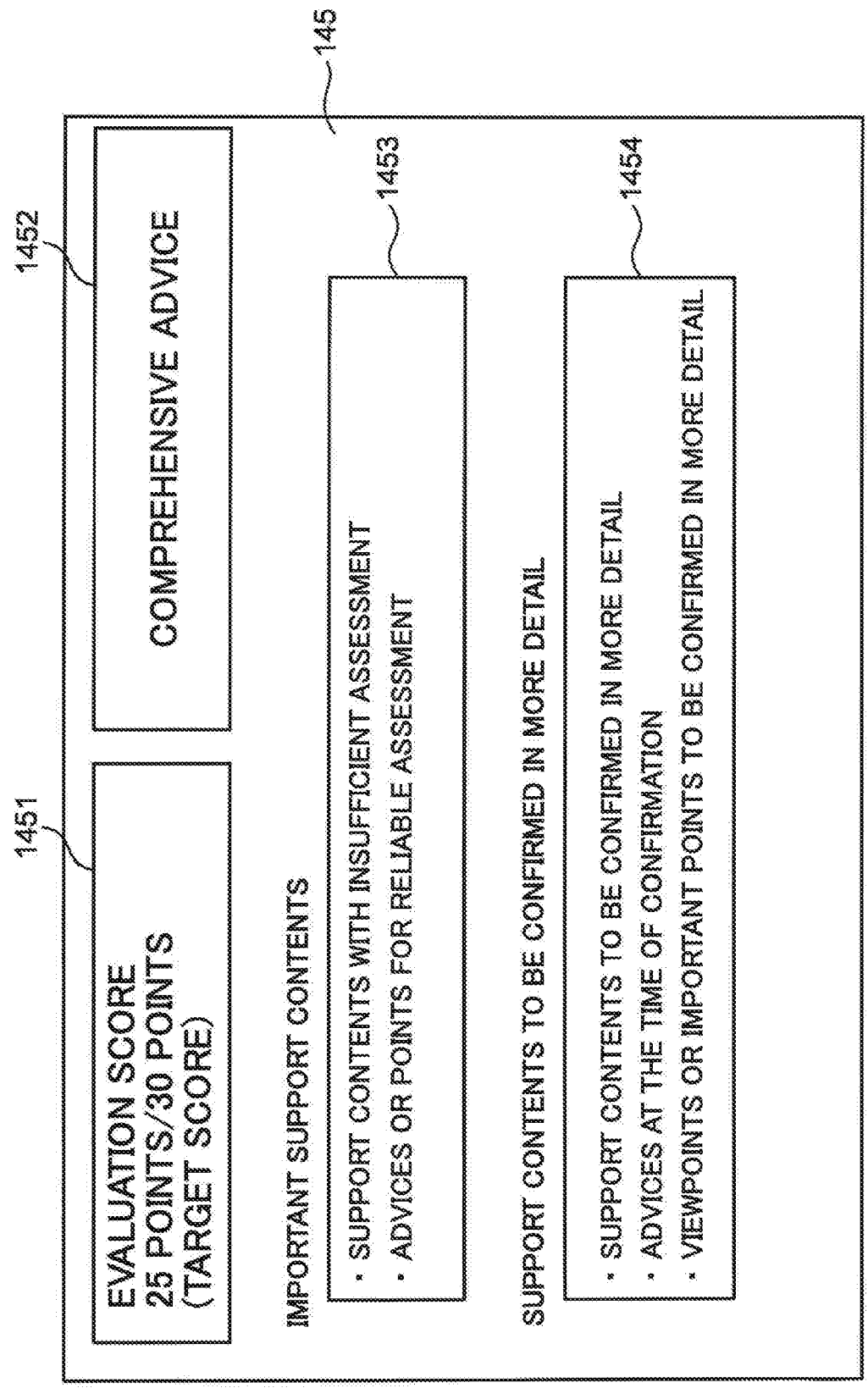
FIG. 11 is a diagram showing an example of an assessment evaluation screen for evaluating assessment by a user in the first embodiment.

FIG. 11 is a diagram showing an example of an assessment evaluation screen evaluating the assessment by the user in the first embodiment. The display unit 14 displays an assessment evaluation screen 145 after the second support content display screen 144 is displayed.

The assessment evaluation screen 145 includes an evaluation score display area 1451 for presenting an evaluation score, an advice display area 1452 for presenting a comprehensive advice to the user, a first support content display area 1453 for presenting the important support content with insufficient assessment and a second support content display area 1454 for presenting the support content to be confirmed in more detail.

The total number of the assessment items of all the second support contents is displayed as a target score in the evaluation score display area 1451, and the number of the assessment items, for which assessment could be made, out of the assessment items of all the second support contents, is displayed as an evaluation score. It is judged that no assessment could be made if an answer "no information/no evaluation" was selected for the assessment item, and it is judged that assessment could be made if an answer other than "no information/no evaluation" was selected.

The second support content including the assessment item, for which no assessment could be made, and advices or points for reliable assessment are displayed in the first support content display area 1453.

Another support content to be confirmed in more detail, advices in confirming the other support content and viewpoints or important points to be confirmed in more detail are displayed in the second support content display area 1454. Note that the other support content may be extracted from a plurality of the first support contents not selected as the second support contents or from the all the support contents. Further, the other support content to be confirmed in more detail may be associated with the support content in advance, and the other support content associated with the second support content may be selected.

Referring back to FIG. 6, subsequently in Step S10, the care plan generator 125 automatically generates the care plan of the care recipient or assistance recipient based on the second support contents determined by the second support content determiner 123. For example, the second support content display screen 144 may include a care plan generation button for instructing the generation of the care plan. If the care plan generation button is depressed by the user, the care plan generator 125 may automatically generate the care plan. The care plan generator 125 outputs the generated care plan to the display unit 14.

Subsequently, in Step S11, the display unit 14 displays the care plan generated by the care plan generator 125.

As described above, according to the first embodiment, the plurality of first support contents corresponding to the care recipient or assistance recipient are first determined from the plurality of support contents based on the basic information on the care recipient or assistance recipient. Subsequently, the second support contents are determined from the plurality of first support contents based on the assessment results input by the user for the assessment items respectively associated with the plurality of first support contents.

Accordingly, the screening of the support contents based on the basic information on the care recipient or assistance recipient and the screening of the support contents based on the assessment results input by the user for the assessment items are performed in two stages. Thus, the support contents more suitable for the care recipient or assistance recipient can be selected and presented.

Next, a monitoring process in the care management support apparatus 1 according to the first embodiment of the present disclosure is described.

Figure 12:
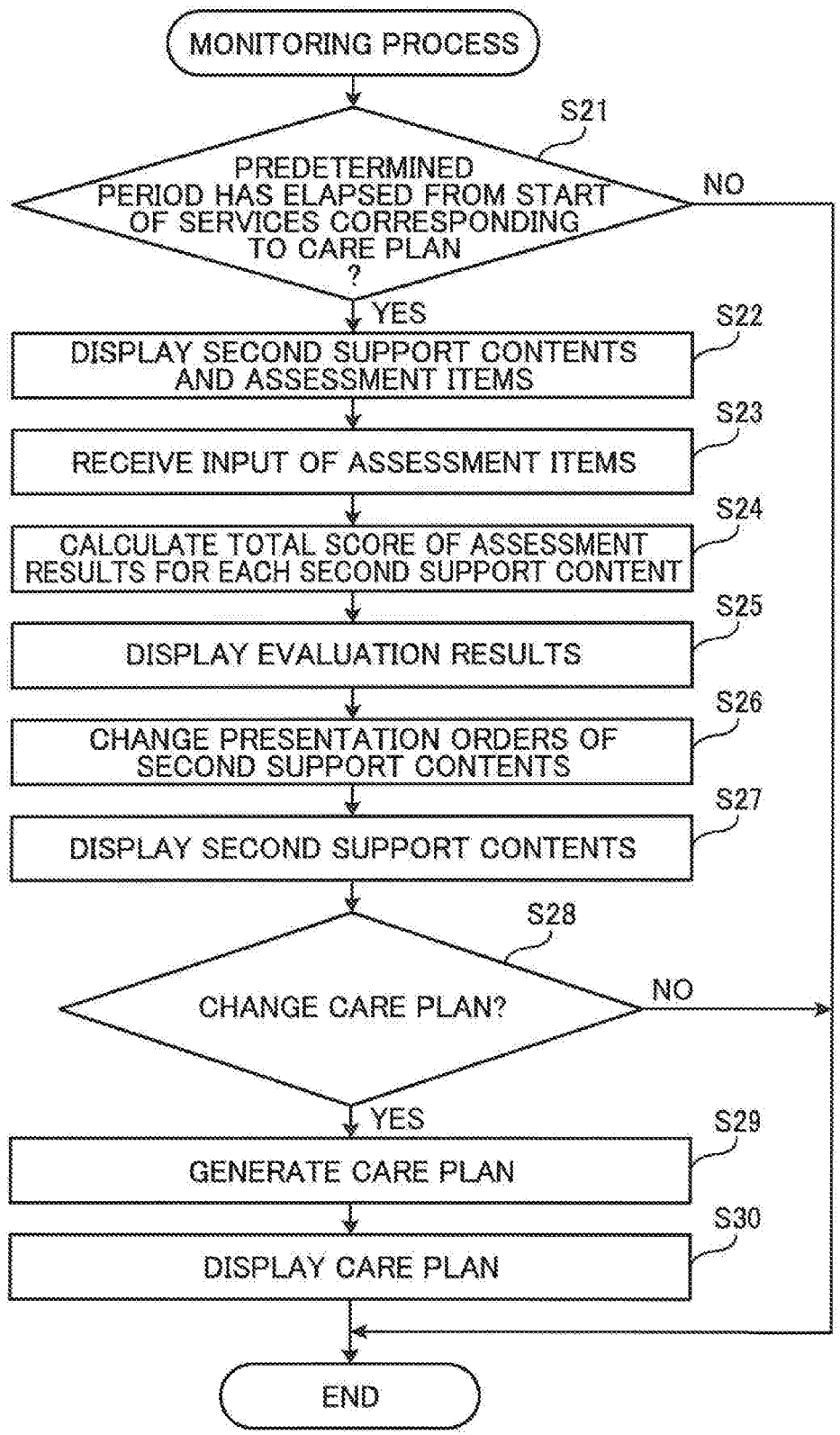
FIG. 12 is a flow chart showing a monitoring process in the care management support apparatus according to the first embodiment of the present disclosure.

FIG. 12 is a flow chart showing the monitoring process in the care management support apparatus 1 according to the first embodiment of the present disclosure. Note that the monitoring process shown in FIG. 12 may be regularly performed, e.g. once a day or may be performed upon receiving a start instruction by the user.

First, in Step S21, the support content evaluator 151 judges whether or not a predetermined period has elapsed from the start of the services corresponding to the care plan. Note that the memory 13 stores information representing the date of starting the services corresponding to the care plan in association with the care plan. The predetermined period is, for example, one week.

Here, if it is judged that the predetermined period has not elapsed from the start of the services corresponding to the care plan (NO in Step S21), the monitoring process is finished.

On the other hand, if it is judged that the predetermined period has elapsed from the start of the services corresponding to the care plan (YES in Step S21), the display unit 14 displays the second support contents used in generating the care plan and the assessment items associated with the second support contents in Step S22. At this time, the support content evaluator 151 outputs the third presentation information for presenting the second support contents and the assessment items associated with the second support contents to the user to the display unit 14.

Subsequently, in Step S23, the input unit 11 receives the input, by the user, of the assessment results for the assessment items associated with the second support contents displayed on the display unit 14. The display unit 14 displays an assessment item display screen for presenting the assessment items associated with the second support contents to the user and receiving the input of the assessment results for the assessment items. The assessment item display screen is the same as the assessment item display screen 143 shown in FIG. 9.

Subsequently, in Step S24, the support content evaluator 151 refers to the score database 133, totals the scores of the assessment results for each second support content and calculates the total score of the assessment results of each second support content. The evaluation result display controller 152 outputs the fourth presentation information for presenting the evaluation results of the second support contents to the user to the display unit 14. Here, the evaluation result of the second support content is the total score of the assessment results of the second support content.

Subsequently, in Step S25, the display unit 14 displays the evaluation results of the second support contents.

Subsequently, in Step S26, the data changer 153 changes the presentation orders of the second support contents used in generating the care plan based on the evaluation results. The data changer 153 outputs presentation information for presenting the second support contents having the presentation orders thereof changed to the user to the display unit 14.

Subsequently, in Step S27, the display unit 14 displays the second support contents having the presentation orders thereof changed.

Subsequently, in Step S28, the care plan change judger 154 judges whether or not to change the care plan based on the evaluation results and the care plan. Here, if it is judged not to change the care plan (NO in Step S28), the monitoring process is finished.

On the other hand, if it is judged to change the care plan (YES in Step S28), the care plan generator 125 automatically generates the care plan for the care recipient or assistance recipient based on the second support contents changed by the data changer 153 in Step S29. The care plan generator 125 outputs the generated care plan to the display unit 14.

Subsequently, in Step S30, the display unit 14 displays the care plan generated by the care plan generator 125.

Note that the care plan generator 125 may receive the input of other pieces of information unique to an individual such as the living form or income of a care plan target person in generating the care plan from the second support contents. In this way, the care plan individualized for the care plan target person can be generated.

Further, the care plan generator 125 may present information on resources of an area where the care plan target person lives (e.g. information representing whether or not there is any facility such as a day-care service facility in the neighborhood or information representing whether or not services such as a meal delivery service can be provided). For example, the care plan generator 125 may present a nursing care facility in a specific area, evaluation/features of this nursing care facility and area services not covered by the long-term care insurance. In this way, the care plan corresponding to area resources can be generated. Further, since the area services not covered by the long-term care insurance can also be recognized, the care management support apparatus 1 can be utilized also in the case of not using the long-term care insurance.

As described above, according to the first embodiment, the second support contents and the assessment items associated with the second support contents are presented to the user after the services based on the care plan generated based on the second support contents are performed for the care recipient or assistance recipient, and the second support contents are evaluated based on the assessment results input by the user for the assessment items.

Accordingly, the second support contents are evaluated based on the assessment results input by the user for the assessment items associated with the second support contents. Therefore, the user can monitor the care plan generated based on the second support contents by confirming the evaluation results of the second support contents.

Second Embodiment

Although the second support contents and the assessment items associated with the second support contents are presented to the user in the monitoring process in the first embodiment, sensor information is obtained and analyzed and an analysis result of the sensor information is presented to the user together with the second support contents and the assessment items associated with the second support contents in a monitoring process in a second embodiment.

Figure 13:
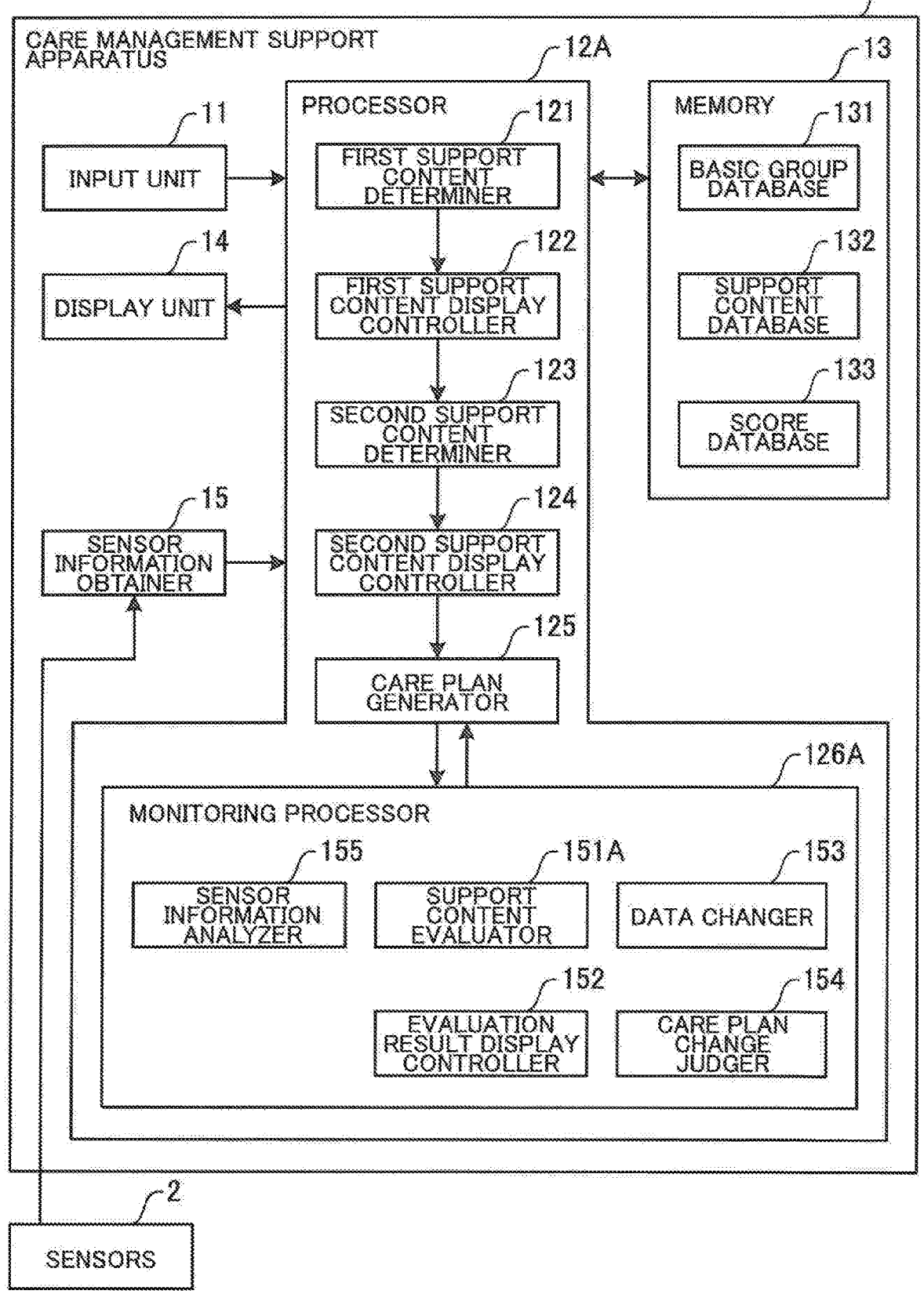
FIG. 13 is a block diagram showing the configuration of a care management support apparatus in a second embodiment of the present disclosure.

FIG. 13 is a block diagram showing the configuration of a care management support apparatus in the second embodiment of the present disclosure. A care management support apparatus 1A is, for example, a personal computer or tablet computer. The care management support apparatus 1A includes an input unit 11, a processor 12A, a memory 13, a display unit 14 and a sensor information obtainer 15. Note that the same components as in the first embodiment are denoted by the same reference signs and not described in the second embodiment.

Sensors 2 are communicably connected to the care management support apparatus 1A via a network. The sensors 2 include, for example, a sensor for measuring a bathroom visit frequency of a care recipient or assistance recipient, a sensor for measuring a body water content of the care recipient or assistance recipient, a sensor for measuring biological information such as a body movement amount, a respiratory rate and a heart rate of the care recipient or assistance recipient and a sensor for measuring the remaining amount of water to be drunk by the care recipient or assistance recipient. The sensors 2 transmit the sensor information to the care management support apparatus 1A. The sensor information is, for example, the bathroom visit frequency of the care recipient or assistance recipient, the body water content of the care recipient or assistance recipient, the biological information such as the body movement amount, the respiratory rate and the heart rate of the care recipient or assistance recipient, and the remaining amount of water to be drunk by the care recipient or assistance recipient.

The sensor information obtainer 15 obtains the sensor information from the sensors 2. The sensor information obtainer 15 has a communication function and receives the sensor information from the sensors 2.

The processor 12 includes a first support content determiner 121, a first support content display controller 122, a second support content determiner 123, a second support content display controller 124, a care plan generator 125 and a monitoring processor 126A.

The monitoring processor 126A includes a support content evaluator 151A, an evaluation result display controller 152, a data changer 153, a care plan change judger 154 and a sensor information analyzer 155.

The sensor information analyzer 155 analyzes the sensor information obtained by the sensor information obtainer 15.

If the sensor information is the bathroom visit frequency of the care recipient or assistance recipient, the sensor information analyzer 155 analyzes a daily excretion frequency of the care recipient or assistance recipient and a predicted daily excretion amount of the care recipient or assistance recipient based on the sensor information.

If the sensor information is the body water content of the care recipient or assistance recipient, the sensor information analyzer 155 analyzes whether or not the body water content of the care recipient or assistance recipient is within a proper range based on the sensor information.

If the sensor information is the biological information such as the body movement amount, the respiratory rate and the heart rate of the care recipient or assistance recipient, the sensor information analyzer 155 analyzes the sleeping time and sleeping state of the care recipient or assistance recipient based on the sensor information.

If the sensor information is the remaining amount of water to be drunk by the care recipient or assistance recipient, the sensor information analyzer 155 analyzes a daily water intake amount of the care recipient or assistance recipient based on the sensor information.

The support content evaluator 151A outputs third presentation information for preventing the analysis result of the sensor information by the sensor information analyzer 155 to the user together with second support contents and assessment items associated with the second support contents. The support content evaluator 151A outputs the third presentation information to the display unit 14.

The display unit 14 displays the analysis result of the sensor information, the second support contents and the assessment items associated with the second support contents when the third presentation information is input from the support content evaluator 151A. The input unit 11 receives the input by a user for the assessment items associated with the second support contents displayed on the display unit 14. At this time, the user can more precisely input answers for the assessment items by confirming the analysis result of the sensor information displayed on the display unit 14.

Note that a system may automatically input the assessment items from the sensor information.

Further, although the sensor information is confirmed and the answer is input for each assessment item in the second embodiment, the sensor information may be confirmed and answers may be input for each support content or for each entry of a care plan.

Further, although the same assessment items as those in the first embodiment are monitored in the second embodiment, monitoring items different from the assessment items may be separately defined.

Further, if an abnormality is judged from the sensor information for such an important assessment item/monitoring item relating to life support, the care management support apparatus may notify this judgment result to the user.

Further, the support content evaluator 151A evaluates the second support contents based on the assessment results input by the user for the assessment items. The support content evaluator 151A converts the assessment results into numerical values and evaluates the second support contents based on the numerical values. Specifically, the support content evaluator 151A refers to the score database 133, totals the scores of the assessment results of the second support contents and calculates the total scores of the second support contents as evaluation results.

Note that a care management support process in the care management support apparatus 1A according to the second embodiment is not described since that is the same as in the first embodiment.

Next, a monitoring process in the care management support apparatus 1A according to the second embodiment of the present disclosure is described.

Figure 14:
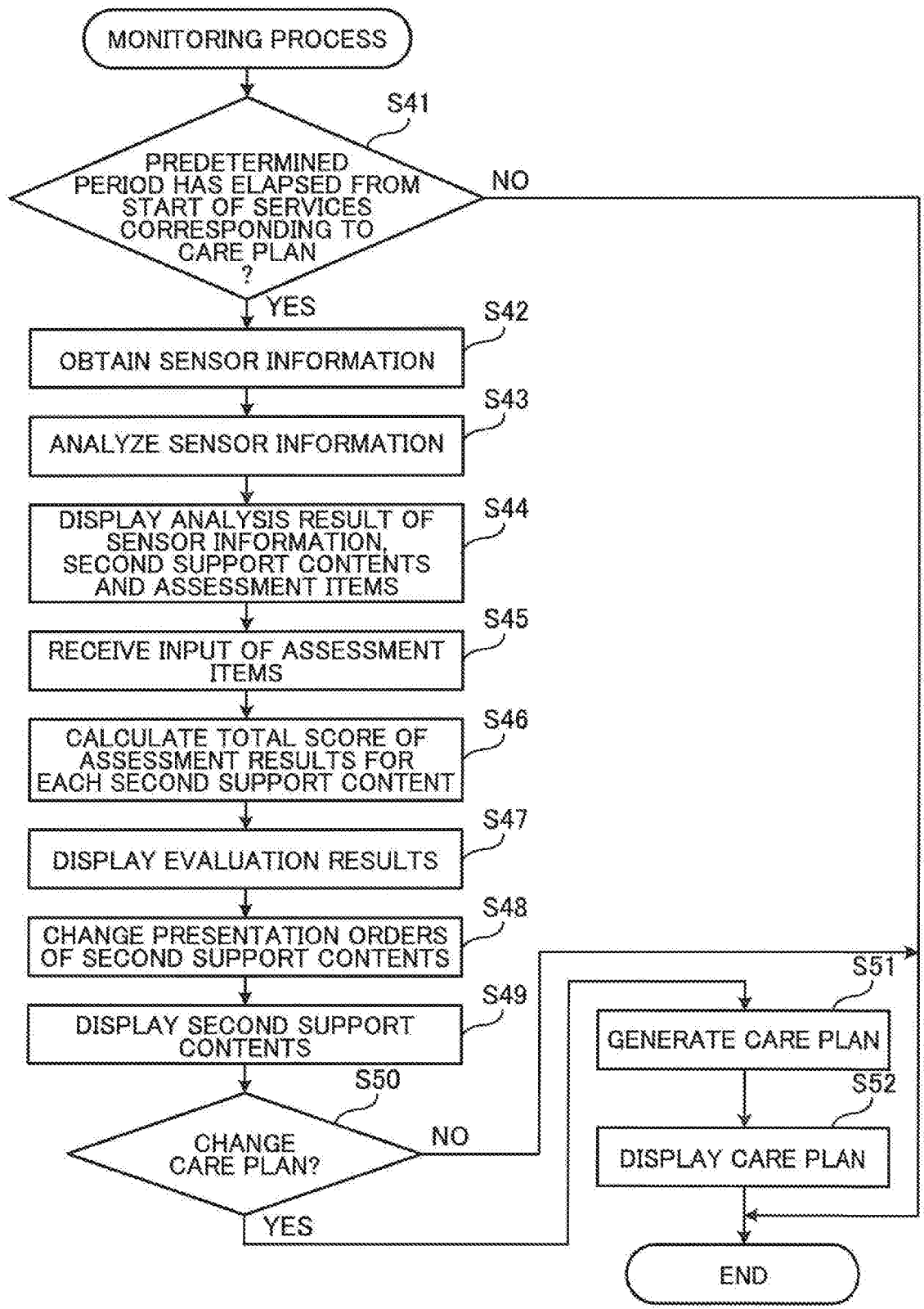
FIG. 14 is a flow chart showing a monitoring process in the care management support apparatus according to the second embodiment of the present disclosure.

FIG. 14 is a flow chart showing the monitoring process in the care management support apparatus 1A according to the second embodiment of the present disclosure. Note that the monitoring process shown in FIG. 14 may be regularly performed, e.g. once a day or may be performed upon receiving a start instruction by the user.

First, in Step S41, the support content evaluator 151A judges whether or not a predetermined period has elapsed from the start of services corresponding to the care plan. Note that the memory 13 stores information representing the date of starting the services corresponding to the care plan in association with the care plan. The predetermined period is, for example, one week.

Here, if it is judged that the predetermined period has not elapsed from the start of the services corresponding to the care plan (NO in Step S41), the monitoring process is finished.

On the other hand, if it is judged that the predetermined period has elapsed from the start of the services corresponding to the care plan (YES in Step S41), the sensor information obtainer 15 obtains the sensor information from the sensors 2 in Step S42. The sensor information obtainer 15 obtains the sensor information for a predetermined period (e.g. one week) accumulated in the sensors 2.

Note that the sensor information obtainer 15 may regularly (e.g. every minute) obtain the sensor information from the sensors 2. In this case, the sensor information obtainer 15 accumulates the regularly obtained sensor information in the memory 13. If it is judged that the predetermined period has elapsed from the start of the services corresponding to the care plan, the sensor information obtainer 15 may obtain the sensor information accumulated in the memory 13.

Subsequently, in Step S43, the sensor information analyzer 155 analyzes the sensor information obtained by the sensor information obtainer 15.

Subsequently, in Step S44, the display unit 14 displays the analysis result of the sensor information, the second support contents used in generating the care plan and the assessment items associated with the second support contents. At this time, the support content evaluator 151A outputs the third presentation information for presenting the analysis result of the sensor information, the second support contents and the assessment items associated with the second support contents to the display unit 14.

Subsequently, in Step S45, the input unit 11 receives the input, by the user, of the assessment results for the assessment items associated with the second support contents displayed on the display unit 14. The display unit 14 displays an assessment item display screen for presenting the analysis result of the sensor information and the assessment items associated with the second support contents to the user and receiving the input of the assessment results for the assessment items.

The processings of Steps S46 to S52 are not described since those are the same as the processings of Steps S24 to S30 of FIG. 12.

As described above, since the analysis result of the obtained sensor information is presented to the user together with the second support contents and the assessment items associated with the second support contents in the second embodiment, the user can more precisely input answers for the assessment items by confirming the analysis result of the sensor information.

Note that, in the second embodiment, the processor 12A may further include a sensor display controller for outputting fifth presentation information for presenting information on the sensors 2 for obtaining the sensor information to the user based on at least either the basic information or the assessment results. The sensor display controller outputs the fifth presentation information to the display unit 14. The display unit 14 displays the information on the sensors 2 when the fifth presentation information is input from the sensor display controller.

For example, if the care recipient or assistance recipient is living alone and his/her cognitive function has declined, the display unit 14 may present a sensor 2 to be arranged at an invisible position in a bathroom to the user and urge the purchase of this sensor 2 to the user. Further, if the care recipient or assistance recipient is living with his/her family and his/her cognitive function has not declined, the display unit 14 may present a sensor 2 to be arranged at a visible position in the bathroom and requiring personal authentication to the user and urge the purchase of this sensor 2 to the user. Further, if the disease information includes vascular brain disease, the display unit 14 may present a sensor 2 capable of measuring more accurate biological information and urge the purchase of this sensor to the user.

Note that although the user is described to be a care manager in each of the above embodiments, the user may be a general user other than a person engaged in the nursing care business. For example, the user may be an aged person to be cared or his/her family. This enables the preparation of a self-care plan and the like. Further, the user may be a person engaged in the medical or nursing care profession other than the care manager, e.g. a visiting care provider or medical professional (doctor, nurse, pharmacist, etc.).

Further, by utilizing the systems according to the embodiments, prefectural and local government officials, care manager associations or the like can confirm how care managers are performing care management for the purpose of educating the care managers.

Further, the systems according to the embodiments may automatically generate the care plan or automate the assessment/monitoring or the like, for example, only based on the sensor information by analyzing care recipient information, assessment items, sensor information, care plan information and the like collected by the systems according to the embodiments.

Note that, in each of the above embodiments, each constituent element may be configured by a dedicated hardware or may be realized by executing a software program suitable therefor. Each constituent element may be realized by a CPU or a program executor such as a processor reading and executing a software program stored in a recording medium such as a hard disk or semiconductor memory.

All or some of functions of the apparatuses according to the embodiments of the present disclosure are typically realized by as an LSI (Large Scale Integration) circuit, which is an integrated circuit. Each of these may be individually realized by one chip or some or all of these may be realized by one chip. Further, circuit integration is not limited to LSI and the functions may be realized by a dedicated circuit or general-purpose processor. An FPGA (Field Programmable Gate Array) or reconfigurable processor capable of reconfiguring the connection and setting of circuit cells inside the LSI may also be utilized.

Further, some or all of the functions of the apparatuses according to the embodiments of the present disclosure may be realized by a processor such as a CPU executing a program.

Further, numbers used in the above are all illustrative to specifically describe the present disclosure and the present disclosure is not limited to the illustrated numbers.

Further, the execution sequences of the respective steps shown in the above flow charts are illustrative to specifically describe the present disclosure and sequences other than the above may be adopted within such a range that similar effects are obtained. Further, some of the above steps may be performed simultaneously with (in parallel with) the other steps.

Since the information processing method, the information processing apparatus and the non-transitory computer-readable recording medium storing an information processing program according to the present disclosure can select and present support contents more suitable for a care recipient or assistance recipient, these are useful as an information processing method, an information processing apparatus and a non-transitory computer-readable recording medium storing an information processing program for outputting presentation information for presenting the support contents for the care recipient or assistance recipient to a user.

Further, with the technique of the present disclosure, more suitable support contents can be presented, whereby not only care specialists, but also people not necessarily having a specialized knowledge such as family members can support, and self-support at home can be realized.

This application is based on U.S. Provisional application No. 62/780,012 filed in United States Patent and Trademark Office on Dec. 14, 2018, Japanese Patent application No. 2019-079145 filed in Japan Patent Office on Apr. 18, 2019 and Japanese Patent application No. 2019-150360 filed in Japan Patent Office on Aug. 20, 2019, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

The invention claimed is:

1. An information processing method performed by a processor of a computer and a display screen of a display, for displaying on the display screen a first list of support services and a second list of support services generated based on assessment results of a user of the apparatus assessing a support recipient's condition after receiving the support services on the first list of support services, comprising:

receiving input data input by the user;
storing in a memory
    a basic group database
        storing basic information including identifying data identifying the support receipt and traits thereof, the mental and physical conditions of the support recipient that cause the need for the support services, and the degree of support needed by the support recipient, and
        associating a plurality of groups of support recipients, each group of support recipients sharing a common trait, with a plurality of mental or physical conditions, and
    a support services database associating
        a plurality of support services assisting the support recipient in performing an activity i) performable without assistance by a fully-functioning person, ii) but performable with difficulty or not performable without assistance by the support recipient, with
        the plurality of groups of support recipients;
determining with the processor a plurality of first support services to be provided to the support recipient by identifying the group of the plurality of groups to which the support recipient belongs, and determining the plurality of first support services based on the physical or mental condition of the group to which the support recipient belongs by referring to the basic group database associating the plurality of groups with a mental or physical condition and by referring to the support services database;
outputting with the processor first presentation information to the display screen to display the first list of support services listing the determined plurality of first support services and to display assessment items, representing an assessment of the condition of the support recipient upon receiving the plurality of first support services and to be inputted by the user, respectively associated with the plurality of first support services to a user;
determining with the processor a predetermined number of the plurality of first support services as second support services to be provided to the support recipient based on the assessment of the condition of the support recipient input by the user upon receiving the plurality of first support services;
outputting with the processor second presentation information to the display screen to display the second list of the support services listing the determined second support services; and
providing the second support services to the user or generating with the processor and displaying on the display screen a care plan for the support recipient in accordance with the displayed second list of support services.

2. An information processing method according to claim 1, wherein the assessment result includes a current state of the support recipient and a future state of the support recipient.

3. An information processing method according to claim 2, wherein:
a processor performs the determining and outputting operations,
the processor
    converts assessment results for each first support service into numerical values, totals the numerical values for each first support service and calculates a total score for each first support service, and determines a predetermined number of the first support services as the second support services for each first support service whose score in the assessment results of the first support services is equal to or larger than a threshold; and assigns a numerical value to a current state of the support recipient when the current state is not assessable by the user, assigns a numerical value to a future state of the support recipient when the future state of the support recipient is not assessable by the user, assigns a numerical value to a current state of the support recipient when the current state of the support recipient is assessable by the user, and assigns a numerical value to a future state of the support recipient when the future state of the support recipient is assessable by the user, and wherein the assigned numerical values for the not assessable current and future states of the support recipient are higher than the assigned numerical values for the assessable current and future states of the support recipient.

4. An information processing method according to claim 1, wherein a processor performs the determining and outputting operations, the processor converts assessment results for each first support service into numerical values, totals the numerical values for each first support service and calculates a total score for each first support service, determines a predetermined number of the first support services as the second support services for each first support service whose score in the assessment results of the first support services is equal to or larger than a threshold.

5. An information processing method according to claim 1, further comprising:

outputting third presentation information for presenting the second list of support services and the assessment item associated with the second support services to the user after a service based on the care plan generated based on the second support services is performed for the support recipient;

evaluating the second support services based on an assessment result input by the user for the assessment item; and outputting fourth presentation information for presenting an evaluation result of the second support services to the user.

6. An information processing method according to claim 5, further comprising:

changing a presentation order of the second support services in the second list of support services based on the evaluation result.

7. An information processing method according to claim 5, further comprising:

determining whether or not to change the care plan based on the evaluation result and the care plan.

8. An information processing method according to claim 5, further comprising:

obtaining sensor information;

analyzing the sensor information; and outputting third presentation information for presenting an analysis result of the sensor information to the user together with the second list of support services and the assessment item associated with the second support services.

9. An information processing method according to claim 8, further comprising:

outputting fifth presentation information for presenting a sensor for obtaining the sensor information to the user based on at least one of the second list of support services information and the assessment result.

10. An information processing method according to claim 1, wherein the plurality of support services stored in the support services database comprise:

basic non-medical support services; and medical support services.

11. An information processing method according to claim 10, wherein the non-medical support services comprise one or more of water-intake support, meal-taking support, oral-hygiene support, and medication-taking support.

12. An information processing method according to claim 1, wherein the displayed care plan lists the types of second support services, the frequency of use of the second support services, and the times for providing the second support services.

13. An information processing method according to claim 1, wherein the displayed care plan displays support resources available in an area where the support recipient lives for providing the second support services.

14. An information processing method according to claim 13, wherein the displayed support resources include one or more of information on whether there is a day-care service facility in the neighborhood of the support recipient, information on whether there is a meal-delivery service available for the support recipient, information on a) whether a nursing-care facility exists in a specific area, b) an evaluation of the nursing-care facility, c) features of the nursing-care facility, and information on support services not covered by long-term care insurance.

15. An information processing method according to claim 1, further comprising:

storing a professional database storing professionals providing the second support services in association with the second list of support services and the assessment items, and displaying on the display screen one of the professionals providing the second support services.

16. An information processing method according to claim 1, wherein the input assessment determines the condition of the support recipient after receiving the first support services and including whether the support recipient is not hindered, hindered, or partially hindered in performing functions performed by the first support services.

17. An apparatus for displaying a first list of support services and a second list of support services generated based on assessment results of a user of the apparatus assessing a support recipient's condition after receiving the support services on the first list of support services, comprising:

an input unit configured to input data by the user;

a processor configured to receive input from the input unit and transmit instructions to the memory;

a memory configured to transmit data to the processor and receive instructions from the processor, the memory including
- a basic group database
  - storing basic information including identifying data identifying the support receipt and traits thereof, the mental and physical conditions of the support recipient that cause the need for the support services, and the degree of support needed by the support recipient, and
  - associating a plurality of groups of support recipients, each group of support recipients sharing a common trait, with a plurality of mental or physical conditions, and
- a support services database associating
  - a plurality of support services assisting the support recipient in performing a physical or mental activity i) performable without assistance by a fully-functioning person, ii) but performable with difficulty or not performable without assistance by the support recipient,
  - with
  - the plurality of groups of support recipients; and
- a display device including a display screen connected to the processor, which controls the displaying of the displays screen,
- wherein the processor
  - determines a plurality of first support services to be provided to the support recipient by identifying the group of the plurality of groups to which the support recipient belongs, and determining the plurality of first support services based on the physical or mental condition of the group to which the support recipient belongs by referring to the basic group database associating the plurality of groups with a mental or physical condition and by referring to the support services database,
  - outputs first presentation information to the display screen for controlling the display screen to display the first list of support services listing the determined plurality of first support services and to display a list of assessment items, representing an assessment of the condition of the support recipient upon receiving the plurality of first support services and to be inputted with the input device by the user, respectively associated with the plurality of first support services to a user,
  - determines a predetermined number of the plurality of first support services as second support services to be provided to the support recipient based on the assessment of the condition of the support recipient input by the user upon receiving the plurality of first support services,
  - outputs second presentation information to the display screen for controlling the display screen to display the second list of the support services listing the determined second support services,
- wherein the second support services are provided to the user or the processor generates and the display screen displays a care plan for the support recipient in accordance with the displayed second list of support services.

18. A non-transitory computer-readable recording medium storing an information processing program for displaying on a display screen a first list of support services and a second list of support services generated based on assessment results of a user of the apparatus assessing a support recipient's condition after receiving the support services on the first list of support services, the program causing a processor of a computer to perform a method comprising:
- receiving input data input by the user;
- storing in a memory
  - a basic group database
    - storing basic information including identifying data identifying the support receipt and traits thereof, the mental and physical conditions of the support recipient that cause the need for the support services, and the degree of support needed by the support recipient, and
    - associating a plurality of groups of support recipients, each group of support recipients sharing a common trait, with a plurality of mental or physical conditions, and
  - a support services database associating
    - a plurality of support services assisting the support recipient in performing an activity i) performable without assistance by a fully-functioning person, ii) but performable with difficulty or not performable without assistance by the support recipient,
    - with
    - the plurality of groups of support recipients;
- determining a plurality of first support services to be provided to the support recipient by identifying the group of the plurality of groups to which the support recipient belongs, and determining the plurality of first support services based on the physical or mental condition of the group to which the support recipient belongs by referring to the basic group database associating the plurality of groups with a mental or physical condition and by referring to the support services database;
- outputting first presentation information on the display screen to display the first list of support services listing the determined plurality of first support services and to display and assessment items, representing an assessment of the condition of the support recipient upon receiving the plurality of first support services and to be inputted with the input device by the user, respectively associated with the plurality of first support services to a user;
- determining a predetermined number of the plurality of first support services as the second support services to be provided to the support recipient based on the assessment of the condition of the support recipient input by the user upon receiving; and
- outputting second presentation information to the display screen to display the second list of support services listing the determined second support services; and
- providing the second support services to the user or generating with the processor and displaying on the display screen a care plan for the support recipient in accordance with the displayed second list of support services.

* * * * *